US00RE34411E

United States Patent [19]

Nishioka et al.

[11] E Patent Number: Re. 34,411

[45] Reissued Date of Patent: Oct. 19, 1993

[54] ELECTRONIC IMAGE PICKUP DEVICE FOR ENDOSCOPES

[75] Inventors: Kimihiko Nishioka; Hisao Yabe, both of Tokyo, Japan

[73] Assignee: Olympus Optical Co., Ltd., Tokyo, Japan

[21] Appl. No.: 658,854

[22] Filed: Feb. 21, 1991

Related U.S. Patent Documents

Reissue of:

[64] Patent No.: 4,807,026
Issued: Feb. 21, 1989
Appl. No.: 28,195
Filed: Mar. 19, 1987

[30] Foreign Application Priority Data

Mar. 19, 1986 [JP] Japan ..... 61-61462

[51] Int. Cl.[5] ..... H04N 7/18; A61B 1/06

[52] U.S. Cl. ..... 358/98; 358/42; 128/6

[58] Field of Search ..... 358/110, 100, 81, 82, 358/113, 98, 42, 44, 209, 211; 359/889-891; 128/4-6

[56] References Cited

U.S. PATENT DOCUMENTS

| | | | |
|---|---|---|---|
| 4,170,987 | 10/1979 | Anselmo et al. | 358/81 X |
| 4,273,110 | 6/1981 | Groux | 128/6 |
| 4,621,284 | 11/1986 | Nishioka et al. | 358/98 |
| 4,653,478 | 3/1987 | Nagasaki et al. | 128/6 |
| 4,695,878 | 9/1987 | Levine et al. | 358/113 X |

FOREIGN PATENT DOCUMENTS

| | | |
|---|---|---|
| 60-247614 | 12/1985 | Japan . |
| 60-262001 | 12/1985 | Japan . |
| 61-159901 | 10/1986 | Japan . |

*Primary Examiner*—Victor R. Kostak
*Attorney, Agent, or Firm*—Cushman, Darby & Cushman

[57] ABSTRACT

An electronic image pickup device for endoscopes is arranged so that at least two filters have mutually different transmitting wavelength ranges are inserted either alternatively or as a rotatable filter disc into an optical path of either an illuminating system or an image pickup system in order to make it possible to obtain either alternatingly or simultaneously color images produced by at least two kinds of rays having mutually different wavelength ranges.

48 Claims, 11 Drawing Sheets

ELECTRONIC IMAGE PICKUP DEVICE FOR ENDOSCOPES

Matter enclosed in heavy brackets [ ] appears in the original patent but forms no part of this reissue specification; matter printed in italics indicates the additions made by reissue.

BACKGROUND OF THE INVENTION (a) Field of the invention

The present invention relates to an electronic image pickup device for endoscopes, which is suitable for being provided in a compact size.

(b) Description of the prior art

There have been proposed in recent years various types of electronic image pickup devices for endoscopes using such devices a solid-state image sensor to serve as an image pickup device.

The above-mentioned electronic image pickup device for endoscopes using a solid-state image sensor has such an advantage that it is capable of preventing the degradation of the quality of images accruing from the breakage of those optical fibers used in an endoscope which employs an image guide formed with an optical fiber bundle, or an advantage that the recording, etc. of the picked-up images becomes easy. Along therewith, a further reduction of size and a further improvement of the resolving power of images to be picked up can be envisaged, so that such an endoscope equipped with an image pickup device made of a solid-state image sensor is going to be used progressively widely from now on.

An electronic image pickup device for endoscopes of the type as mentioned above which is disclosed in, for example, Japanese Utility Model Preliminary Publication No. Sho 61-159901 provides an apparatus characterized by comprising an endoscope equipped with a line-sequential transmission type solid-state image sensor which is disposed within the forward end portion of the endoscope to be operative so as to receive an optical image coming from an object under observation and to convert the optical image thereof to an electric signal, and also equipped with a light-transmitter which receives, at its light-incidence end face, the light coming from a light source and which leads this light to a light-emitting end face thereof provided at the forward end portion of the endoscope to thereby illuminate the object under observation, and further comprising a filter disc disposed between said light source and the light-incidence end face of said light transmitter and having, formed on a same circumferential face in an alternating fashion, a light-blocking area for blocking the light beam coming from the light source and also having light-beam-transmitting areas for transmission therethrough of at least three different kinds of color lights, respectively, whereby the apparatus is operative so that, by rotating the filter disc at a constant speed, said at least three different kinds of color lights will successively illuminate the object under observation with an interval of time corresponding to the light-blocking period between respective such illuminations, thereby reading out during each light-blocking period the electric charge accumulated in said solid-state image sensor and converting the thus read-out electric charge to an electric signal, to perform a display of a color image of the object under observation based on such electric signals. In addition, the apparatus is further characterized in that the opposing ends of said light-transmitting areas and the diaphragm which is provided on the light-source side away from said light transmitter are each formed to have such a configuration that a constant time period of passage of the light-blocking area can be maintained during the revolutions of the filter disc for those light beam-transmitters which could have different diameters.

However, the above-described conventional electronic image pickup device for endoscopes is exclusively aimed to perform observations by the use of only visible light, and thus it has been impossible to conduct observations utilizing invisible light.

SUMMARY OF THE INVENTION

It is, therefore, a primary object of the present invention to provide, in view of the above-stated circumstances, an electronic image pickup device for endoscopes, which makes it possible to perform observations under rays of mutually different two or more wavelength ranges such as visible light and invisible rays.

According to the present invention, the above-mentioned objected is attained by arranging two or more filters having mutually different properties either in alternatingly insertable fashion or rotatably in the optical path of either the illuminating system or the image pickup system, to allow the observation, either alternatingly or simultaneously, of the images formed by rays of two or more wavelength ranges.

Another object of the present invention is to provide an electrode image pickup device for endoscopes, which is arranged to allow the observation of an object for study in the form of a color image.

Still another object of the present invention is to construct the endoscope of the above-mentioned type in as much a compact size as possible.

According to a preferred formation of the present invention, arrangement is provided so that, between the light-incidence end of a light guide and a light source, there are disposed an infrared light removing filter and a visible light removing filter in a mutually alternatingly insertable fashion, whereby when the infrared light removing filter is inserted in the optical path, there is obtained a color image formed by the visible light, whereas when the visible light removing filter is used, a false color image is obtained.

According to another preferred formation of the present invention, the above-mentioned infrared light removing filter and visible light removing filter are provided on a same circumference to form a rotatable filter, so that a color image by visible light and a false color image by infrared light can be displayed simultaneously on two television monitoring screens.

According to still another preferred formation of the present invention, arrangement is provided so that said infrared light removing filter and said visible ray removing filter are disposed in an alternatingly insertable and removable fashion in the optical path of a television camera mounted on the eyepiece portion of the fiberscope of the endoscope, or that in place of the above, said rotatable filter alone is disposed in said optical path, whereby making it possible to display a color image by visible light and a false color image by infrared light either in an alternating fashion on a single TV monitoring screen, or simultaneously on two separate TV monitoring screens.

These and other objects as well as the features and advantages of the present invention will be apparent from the following detailed description of the preferred embodiments when taken in conjunction with the accompanying drawings and appended claims.

DETAILED DESCRIPTION OF THE PREFERRED EMBODIMENTS

Description will hereunder be made of the present invention based on the illustrated embodiments.

Figure 1:
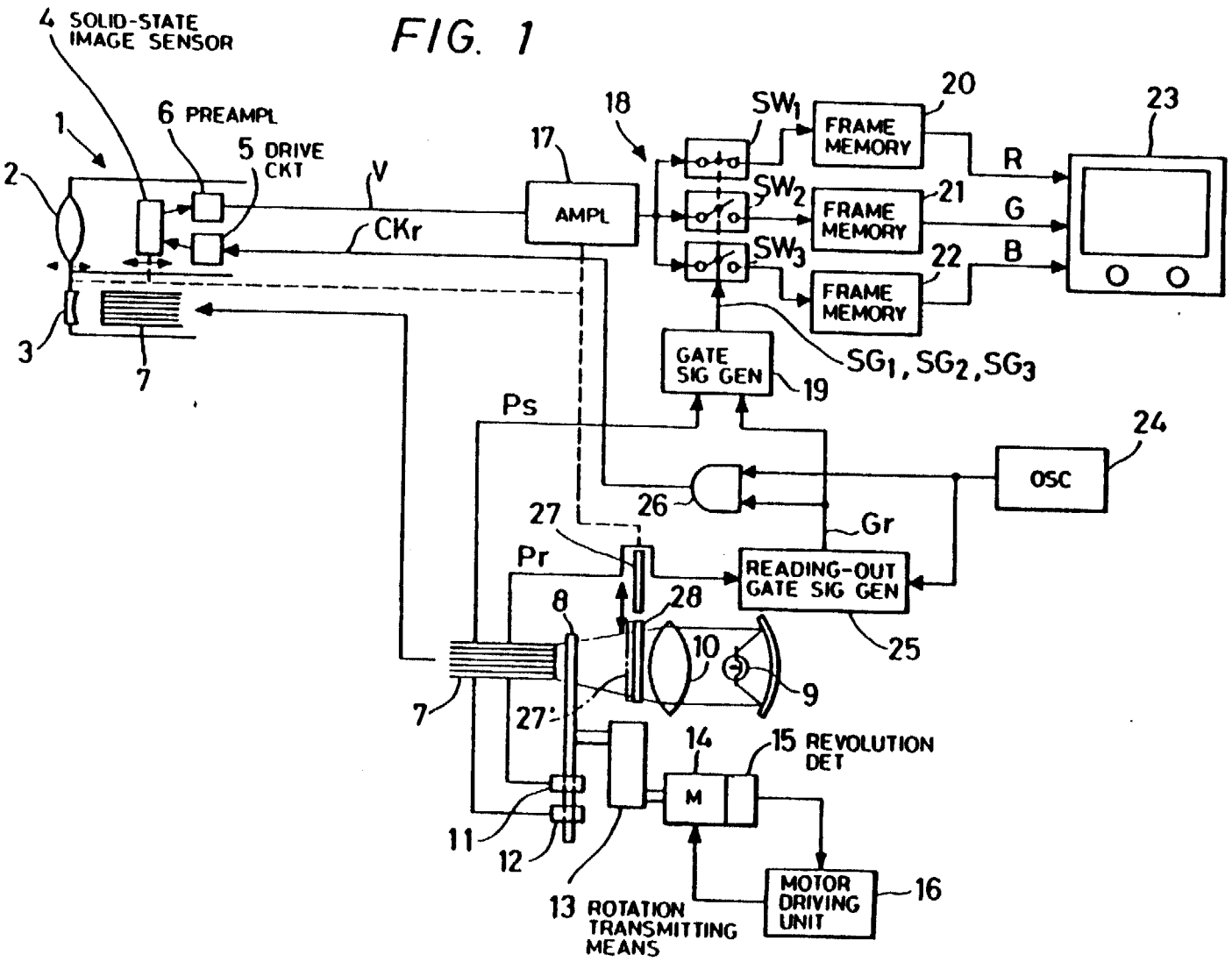
FIG. 1 is a block diagram showing the arrangement of a first embodiment of the electronic image pickup device for endoscopes according to the present invention.
Figure 2:
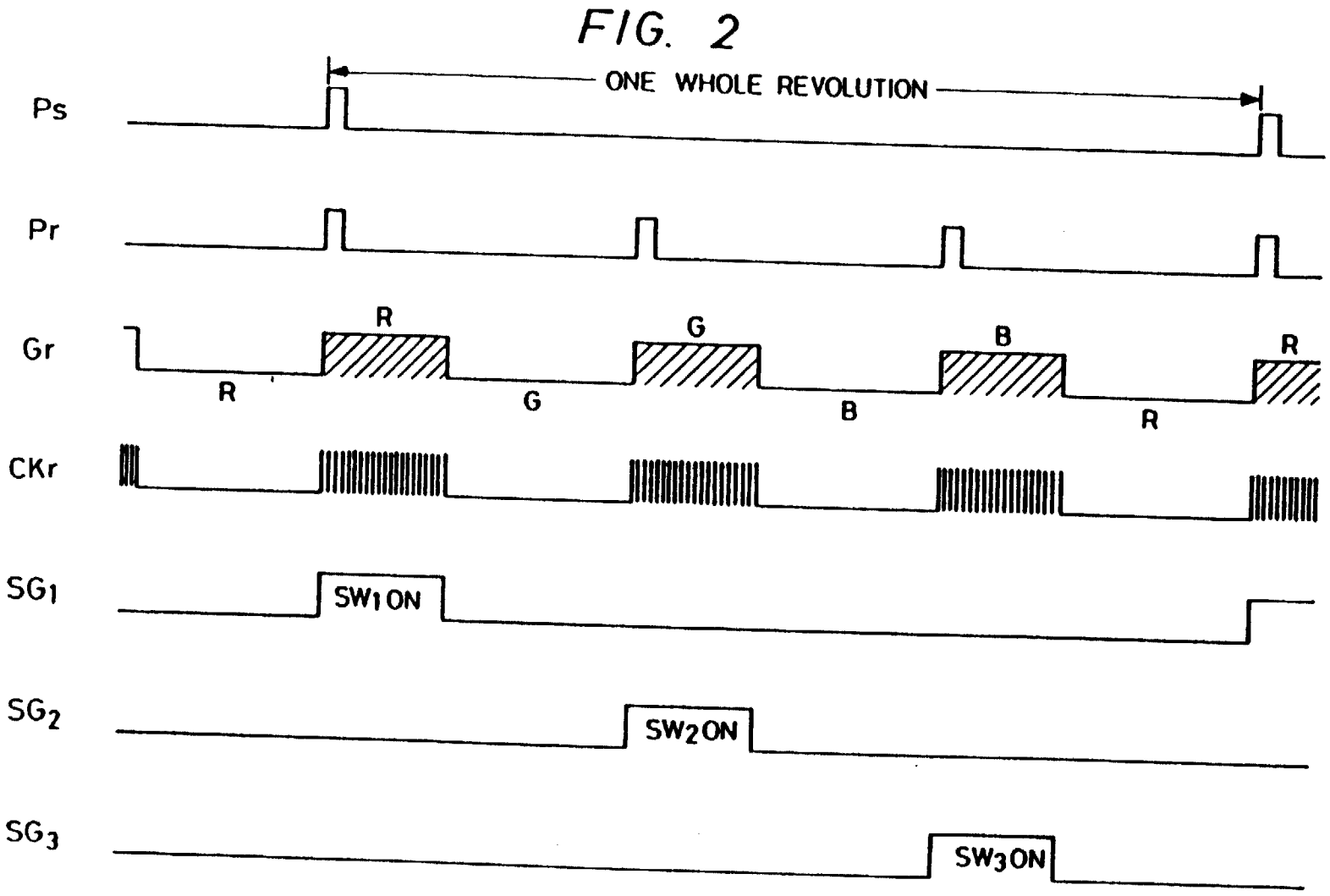
FIG. 2 is a timing chart showing the operation of said first embodiment.

FIG. 1 is a block diagram showing the construction of the first embodiment of the electronic image pickup device for endoscopes according to the present invention. FIG. 2 is a timing chart for explaining the operation thereof. It should be noted that three or more different kinds of color lights may herein be the lights of the four kinds of colors which are red, green, blue and yellow, or they may be the color lights of complementary colors such as cyan, yellow, magenta, etc. The following description will be made, however, with respect to the instance of the three kinds of color lights, i.e. red, green and blue.

In FIG. 1, reference numeral 1 denotes the forward end portion of an endoscope. At the foremost end thereof, there are disposed an objective lens 2 and an illuminating lens 3 which are arranged in parallel. Behind the objective lens 2 is provided a solid-state image sensor 4 of the line-sequential transfer type which converts the optical image of the received light to an image signal V by a drive circuit 5, and transfers this image signal V, via a preamplifier 6, to the circuitry of the next stage. In the background of the illuminating lens 3, there is disposed a light guide 7 formed by, for example, an optical fiber bundle. This light guide 7 is so arranged that an illuminating light is irradiated onto the light-incidence end face of the light guide via a rotatable filter 8. The illuminating light is emitted from a light source lamp 9, and after passing through a lens 10, it impinges onto the rotatable filter 8. This illuminating light is caused to impinge onto the end face of said light guide 7 via the filters for R (red), G (green) and B (blue) which are disposed on the filter disc 8 in successive order with an appropriate light-blocking interval interposed between these respective color filters. The filter disc 8 has its rotary axis which is coupled to a motor 14 via rotation-transmitting means 13. A motor driving unit 16 is controlled by a signal supplied from a revolution detector 15 provided on the motor 14, to keep the revolution speed of the motor at a constant value. Also, on the outer circumferential portion of the filter disc 8, there are provided timing detectors 11 and 12 for generating a reading-out pulse, a start pulse, etc. to thereby establish a synchronism between such actions as the reading-out of informations from the solid-state image sensor 4 and the revolution of the filter disc 8. On the other hand, the image signal V from said preamplifier 6 is further passed through an amplifier 17 for its amplification, and the resulting signal is inputted to a multiplexer 18. This multiplexer 19 is comprised of three switches $SW_1$, $SW_2$ and $SW_3$ corresponding to the signals R, G and B, respectively, which are inputted thereto. These switches are changed-over of their connections successively with a predetermined frame cycle by gate signals $SG_1$, $SG_2$ and $SG_3$ intended for these respective switches, which signals being delivered from a multiplexing gate signal generator 19 to thereby supply to respective R, G and B frame memories 20, 21 and 22 those image signals which correspond to the respective colors. The respective color signal which have been stored in the respective frame memories are read out and synthesized and the resulting signal is displayed in color by a color TV monitor 23. In the above-described construction, the reading-out pulse detector 11 is intended to detect the terminal end positions of the respective filters for R, G and B which are arranged on the filter disc 8 to be arrayed in the direction of revolution of this filter disc 8, and this detector is operative so as to use its detected pulse (reading-out pulse) Pr and a signal supplied from an oscillator 24 to form a reading-out gate signal Gr. This reading-out gate signal Gr is one intended for reading out, during the periods corresponding to the periods of time in which the lights R, G and B are not irradiated onto the solid-state image sensor 4, the image signal which has been accumulated in this solid-state image sensor 4. This signal, along with a signal delivered from the oscillator 24, is inputted into an AND circuit 26 to thereby form a reading-out clock signal CKr which, in turn, drives said driver circuit 5 whereby to convert the electric charge accumulated in the solid-state image sensor 4 to an image signal V for each of the colors R, G and B. On the other hand, said reading-out gate signal Gr, together with a detection pulse (start pulse) supplied from said start pulse detector 12 (which is intended to detect one whole revolution of the filter disc 8), is inputted to the multiplexing gate signal generator 19 to form gate signals $SG_1$, $SG_2$ and $SG_3$ intended for the abovesaid respective switches, to thereby changeover the connection of the multiplexer 18 so as to input an image signal to the respective frame memories 20, 21 and 22 for R, G and B, respectively.

With such a construction as described above, it will be noted that, for every one revolution of the filter disc 8, one start pulse Ps is outputted to be delivered to the multiplexing gate signal generator 19, and also, for each one whole revolution of the disc 8, three reading-out pulses Pr corresponding to the R, G and B filters, respectively, are outputted to be sent to a reading-out gate signal generator 25. This reading-out gate signal generator 25 uses the signal coming from the oscillator 24 to form a reading-out gate signal Gr which is synchronous with the reading-out pulse Pr and has a width corresponding to the period of time in which each of the lights R, G and B is not irradiated. Based on this period of time of the reading out gate signal Gr, there are formed a reading-out clock signal CKr and also switching gate signals $SG_1$, $SG_2$ and $SG_3$ whereby to obtain R, G and B signals which are necessary for color display. In the illustrated reading-out gate signal Gr, those hatched regions represent the periods for reading out the R, G and B image signals, respectively. Those low-level periods located at positions preceding the respective hatched regions represent the periods of time in which electric charges for R, G and B signals are accumulated in the solid-state image sensor 4 due to the irradiation of R, G and B lights. Accordingly, the switching gate signals $SG_1$, $SG_2$ and $SG_3$ for the R, G and B frame memories 20, 21 and 22 will be rendered to become gate signals corresponding to the R, G and B image signal reading-out periods, respectively.

Figure 3:
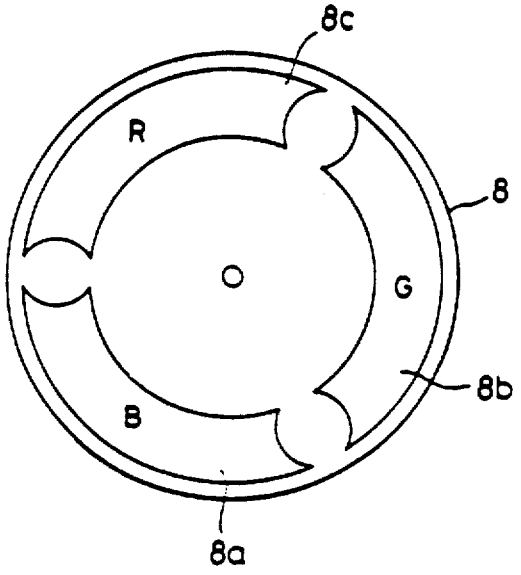
FIG. 3 is a front view of the rotatable filter of said first embodiment.

Here, the filter disc 8 is constructed as shown in, for example, FIG. 3. That is, it is constituted by arranging, on a same circumference, those filters 8a, 8b and 8c which have such spectral transmittances as A, B and C shown in FIG. 4. It should be noted here that the shapes of the respective opposing end portions of the filters 8a, 8b and 8c are each formed to have an arcuate shape to match the cross sectional shape of the light bundle. Numerals 27 and 28 represent an infrared light removing filter and a visible light removing filter which can be alternatively inserted between the light-incidence end of the light guide 7 and the lens 10. Their spectral transmittances are as shown in FIG. 5.

The electronic image pickup device for endoscopes according to the present invention are arranged as described above. Accordingly, when the infrared light removing filter 27 is inserted in the optical path, there is obtained a color image formed by an ordinary visible light, whereas when the visible light removing filter 28 is inserted in the optical path, there is obtained a false color image formed by dividing the infrared light range into three wavelength ranges $I_1$, $I_2$ and $I_3$. As shown by a chain line in FIG. 1, arrangement may be provided so that a separate infrared light removing filter 27' is bonded to the visible light removing filter 28 to thereby obtain a color image formed by a visible light and a false color image formed by an ultraviolet light.

Also, as shown by dotted lines in FIG. 1, arrangement may be made so that the gain of the amplifier 17 is altered interlockingly with the inter-changed assembly of the infrared light removing filter 27 and the visible light removing filter 28, to thereby perform an adjustment of sensitivity to light. Also, the gain of the amplifier 17 may be changed for each of the three wavelengths in the infrared range. This latter arrangement is utilized to perform compensation of the difference occurring in the intensity of light where the light source lamp 9 is of the type whose intensity of light can vary depending on the wavelength range as noted in case of a xenon lamp.

Figure 4:
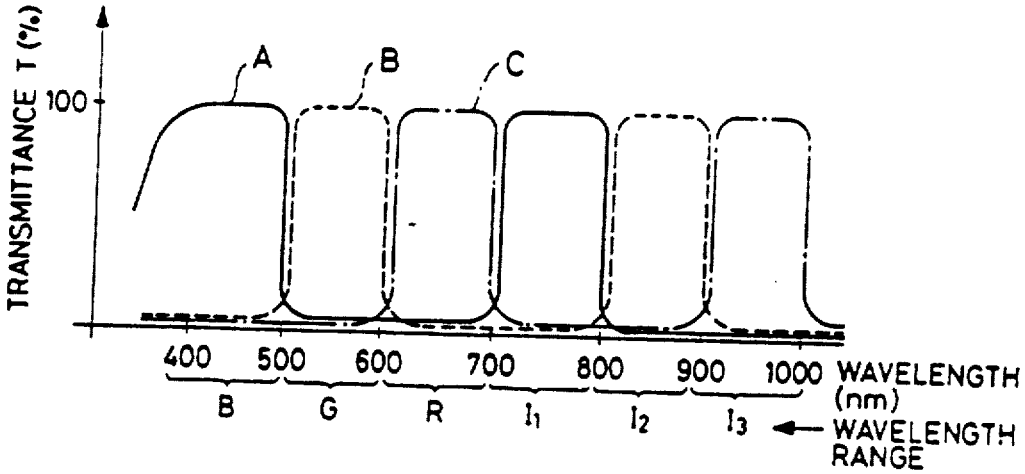
FIG. 4 is an illustration showing the spectral transmittance of the rotatable filter of said first embodiment.
Figure 5:
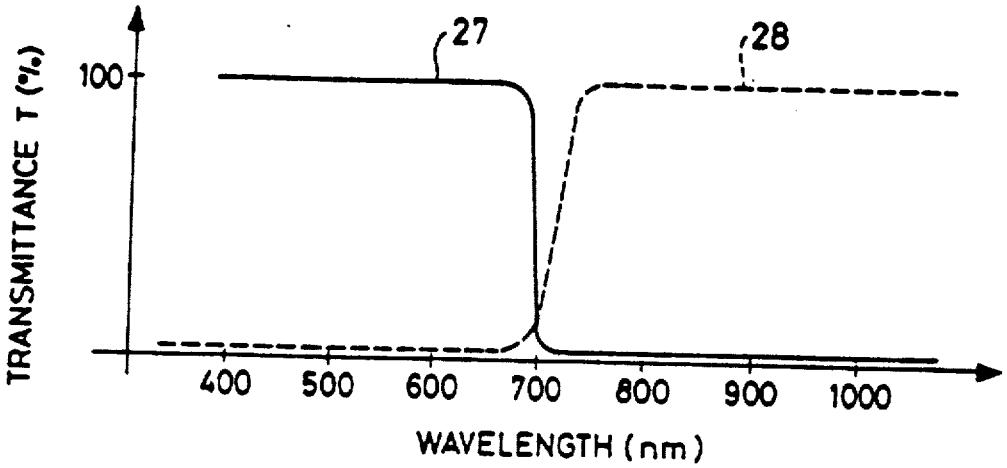
FIG. 5 is an illustration showing the spectral transmittance of the infrared light removing filter and that of the visible light removing filter of the above-mentioned embodiment.
Figure 6:
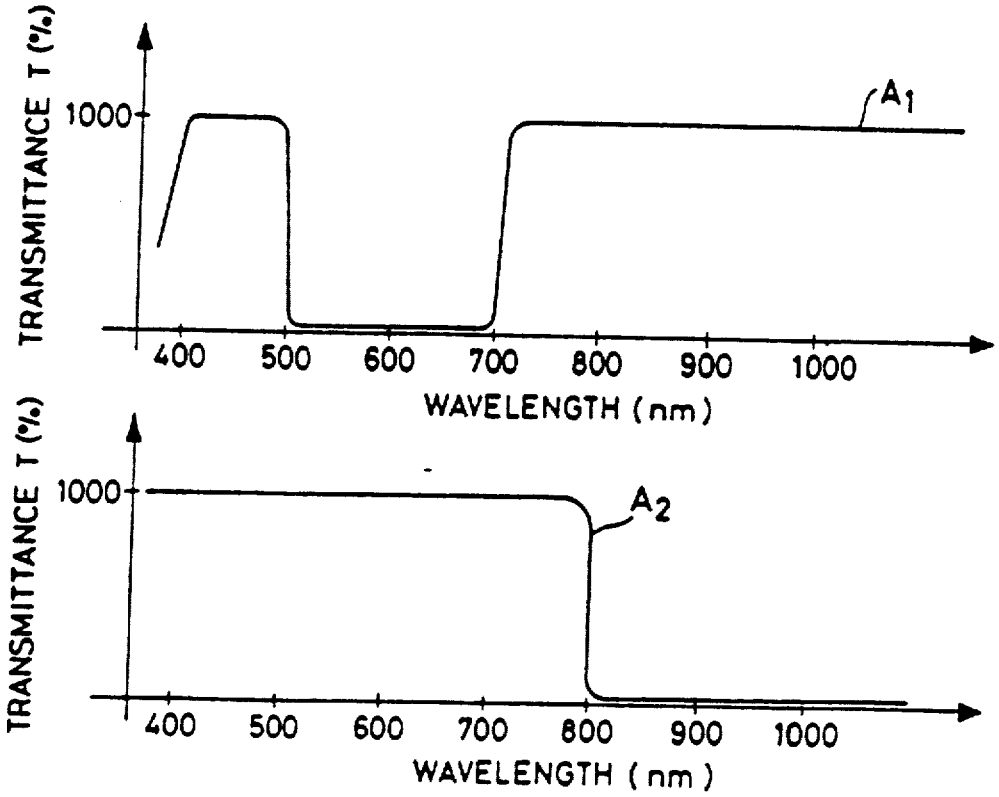
FIG. 6 is an illustration showing the spectral transmittance of the assembled filter in case the filter of FIG. 4 is formed by a superposing technique.

Also, a filter having the property as shown in FIG. 4 may be formed by vapor-deposition of an interference film, or otherwise there may be formed a filter having such a property as A of FIG. 4 by superposing a filter having such a property as $A_1$ in FIG. 6 upon a filter having a property such as $A_2$.

Also, as shown by dotted lines in FIG. 1, it would be better to arrange so that the inter-changed arrangement of the filter 27 and the filter 28 relative to each other is interlocked with either the objective lens 2 or the image sensor 4 to shift the focal position of the solid-state image sensor 4 in synchronism with the change-over between the observation under visible light and the observation under infrared light. That is, in case of an observation under infrared light, in general, the focal position shifts rearwardly as compared to the observation under visible light. Therefore, it is only necessary to shift at least either one of the objective lens 2 and the solid-state image sensor 4 in a direction in which these two members are parted away from each other, when the observation is switched over to that performed under infrared light.

Figure 7:
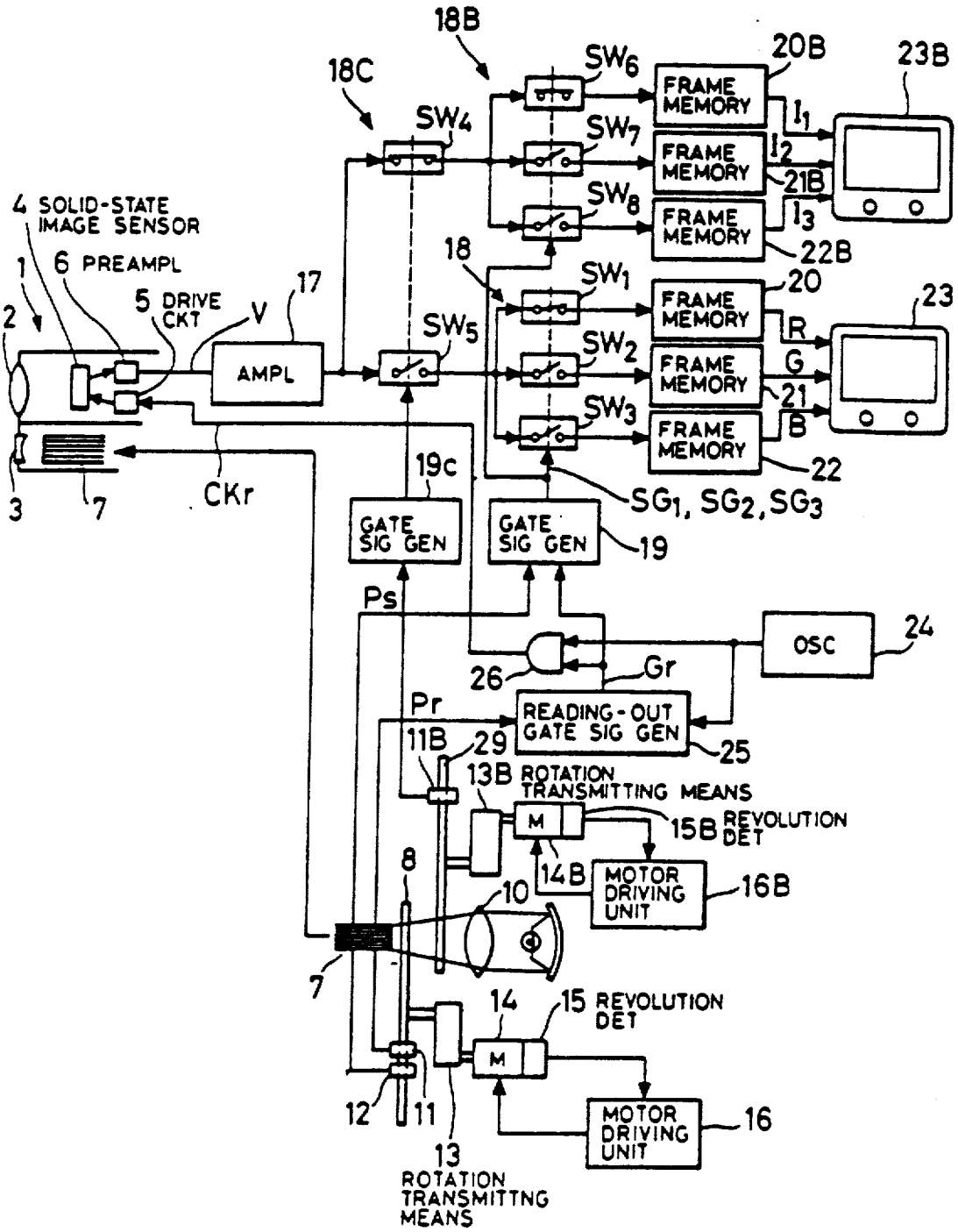
FIG. 7 is a block diagram showing the construction of a second embodiment.
Figure 8:
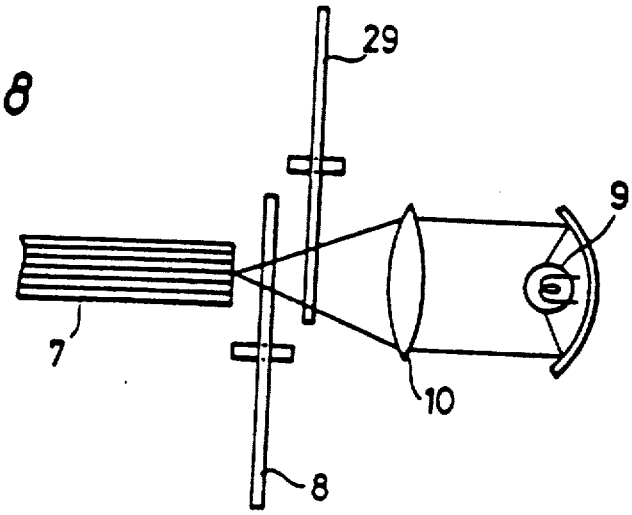
FIG. 8 is an enlarged diagram of the essential part of said second embodiment.
Figure 9:
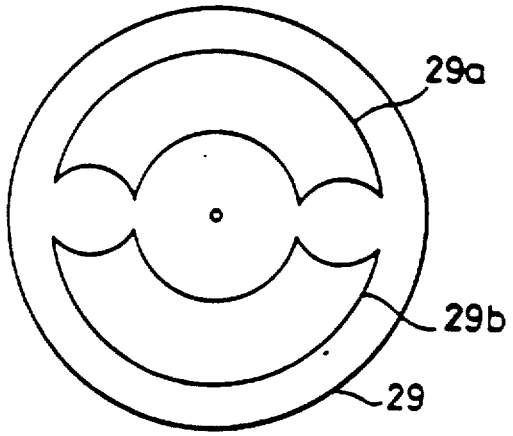
FIG. 9 is a front view of the rotatable filter of said second embodiment.

FIG. 7 is a block diagram showing the construction of the second embodiment. This embodiment uses, as shown in FIG. 9, a filter disc 29 which is comprised of a filter 29a having the property of the infrared light removing filter 27, and also comprised of a filter 29b having the property of the visible light removing filter 28, both of these two filters being arranged on a same circumference, and the resulting filter disc 29 is disposed between the light-incidence end of the light guide 7 and the lens 10 in such a manner as shown in FIG. 8, and this filter disc 29 is rotated at a revolution rate of ½ of that of the filter disc 8. It should be noted here that the configurations of the respective opposing end portions of these two filters 29a and 29b are each formed in an arcuate shape to conform to the cross sectional configuration and size of a light bundle.

In FIG. 7, numeral 11B represents a reading-out pulse detector for the filter disc 29; 13B a transmitting means for coupling the rotary axis of the rotatable filter disc 29 to a motor 14B; 15B a revolution detector provided on the motor 14B; a motor driver which is controlled by a signal coming from the revolution detector 15B; 18B a multiplexer which is comprised of three switches $SW_6$, $SW_7$ and $SW_8$ corresponding to the inputted signals R, G and B; 18C a duplexer comprised of two switches $SW_4$ and $SW_5$ which are changed-over of their connections by a gate signal supplied from a duplexing gate signal generator 19C connected to the reading-out pulse detector 11B. The two multiplexers 18 and 18B are caused by the duplexer 18C to be operated in an alternating fashion. Numerals 20B, 21B and 22B are frame memories for other R, G and B; and 23B another color TV monitor.

According to this second embodiment, it will be noted that, by changing-over the signals which are to be delivered to the two TV monitors 23 and 23B in synchronism with the revolution of the rotatable filter disc 29, it is possible to simultaneously display a visible light color image on the screen of one of the two TV monitors 23 and 23B, while displaying an infrared light false color image on the screen of the other one of these monitors.

Figure 10:
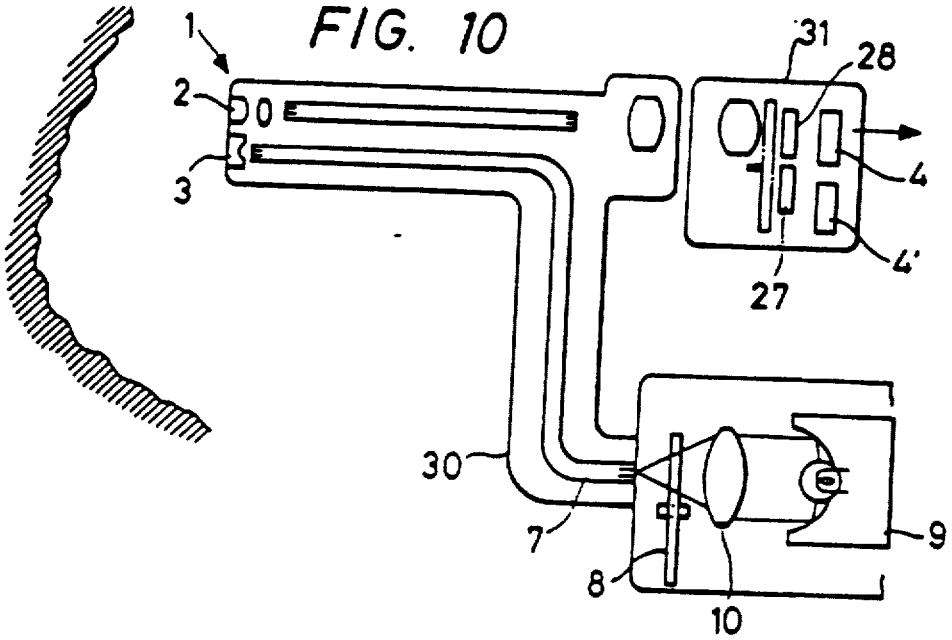
FIGS. 10 to 12 are illustrations showing the constructions of the third to fifth embodiments, respectively.

FIG. 10 shows the construction of a third embodiment, which is such that a TV camera 31 of the color-sequential system is mounted on the eyepiece portion of a fiberscope 30. This arrangement is operative in such a way that, by alternatively inserting the infrared light removing filter 27 and the visible light removing filter 28 in the optical path in the TV camera 31, it is possible to selectively display, on the screen of the TV monitor, a visible light color image or an infrared light false color image. In place of the above-described arrangement of the two filters 27 and 28, a rotatable filter disc 29 may be mounted for revolution as indicated by the chain line, making it possible to perform simultaneous display of the visible light color image and the infrared light false color image on the screens of the two TV monitors, respectively, as in the case of the second embodiment shown in FIG. 7.

It should be noted here that, in place of the fiberscope 30, a rigid lens assembly may be used. Also, jointly with the solid-state image sensor 4, a second solid-state image sensor 4' having a different light-sensitive wavelength range may be disposed also within the camera in such a way that these two image sensors 4 and 4' are to be alternatively inserted in the optical path thereof. In such an instance, a convenience is obtained from the provision of an arrangement allowing slidable movement of these image sensors in the camera.

Figure 11:
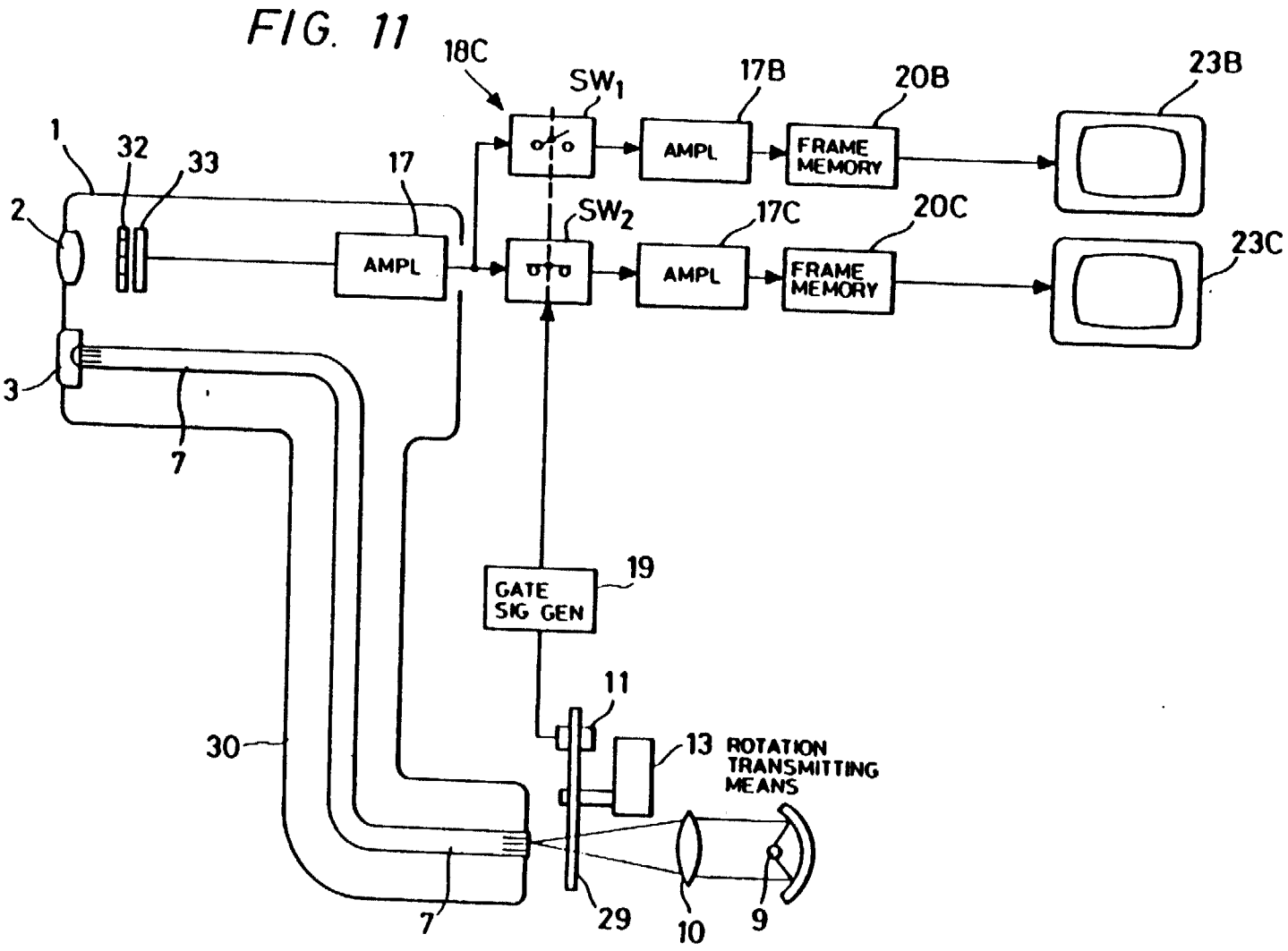

FIG. 11 shows the construction of a fourth embodiment. This instant embodiment shows an electronic endoscope of the color image pickup system, being equipped with a rotatable filter disc 29 which performs changeover between visible light and infrared light as shown in FIG. 9, and using, on the light-incidence face side, a solid-state image sensor 33 having a color-separating mozaic filter 32 (for the simultaneous system) to serve as an image pickup means. This mozaic filter 32 has a spectral transmittance as shown in FIG. 4. Numerals 17B and 17C represent amplifiers; 20B and 20C memories; 23B and 23C color TV monitors. By using this device in such a way that the revolution of the rotatable filter disc 29 is detected to thereby effect changeover between two signal processing systems by means of the switches $SW_1$ and $SW_2$ in synchronism with the changeover occurring between visible light and infrared light, it is possible to perform simultaneous display of the visible ray image and the infrared ray image in a manner similar to that of the instance shown in FIG. 7.

As the signal processing circuitry, those which are employed in ordinary one-CCD (charge-coupled device) color cameras can be utilized in the respective constituent systems without requiring any modification thereof. It should be noted there that the memories which are to be used in this instance have no such function as to synchronize the image signals of respective colors which are obtained sequentially as in the case of areasequential color television system. Instead, this circuitry need only to possess the function of holding the image throughout the interval of time required for the change of timing between the image sensor and the CRT and up to the arrival of the next image signal.

Figure 12:
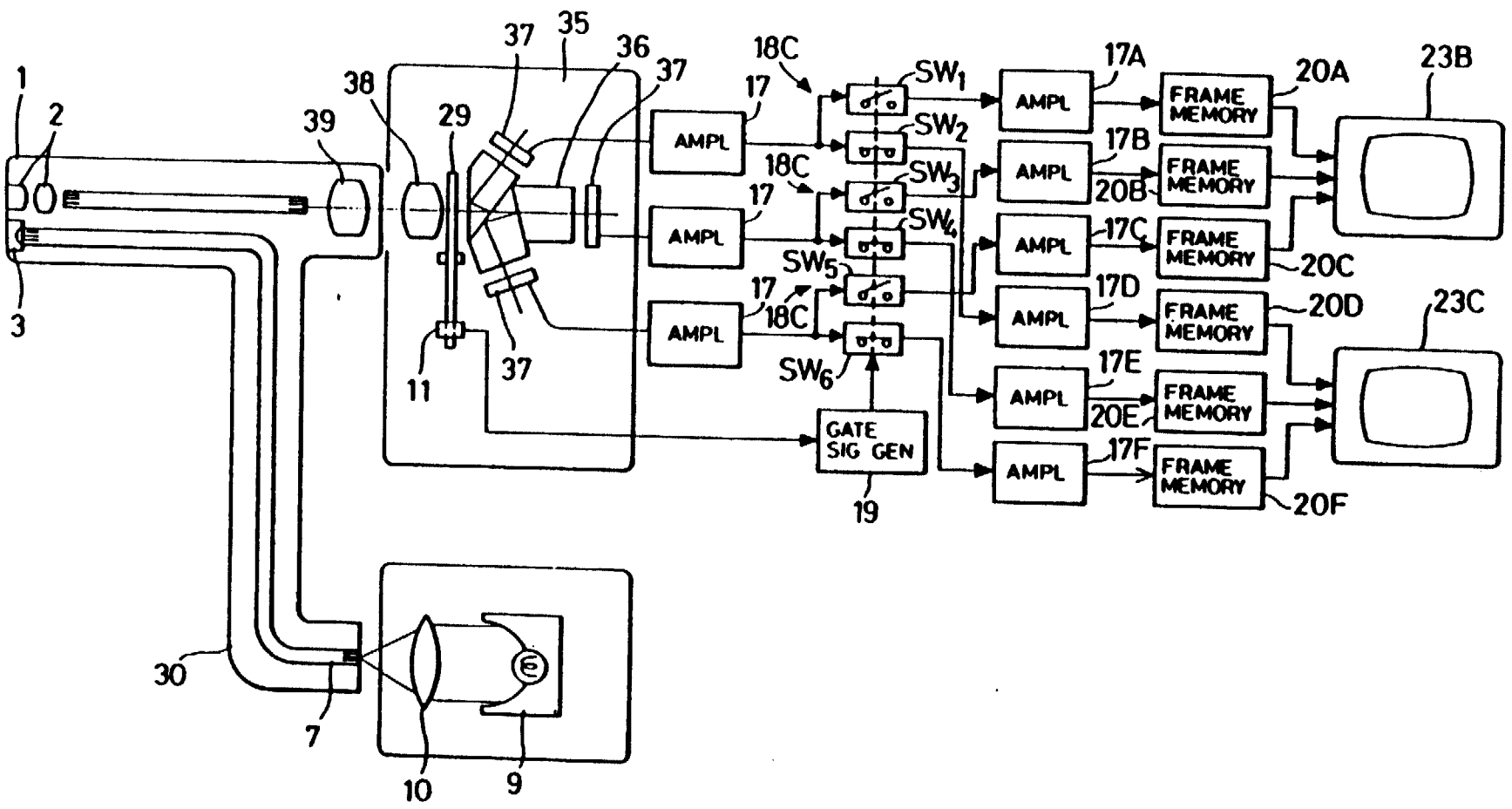

FIG. 12 shows the construction of a fifth embodiment. This embodiment is such that a rotatable filter disc 29 similar to that shown in FIG. 11 is disposed within either a 3-CCD TV camera or a 3-tube TV camera 35. Numeral 36 represents a three-color spectroscopic prism; 37 a solid-state image sensor or an image pickup tube; and 39 an ocular lens. Numerals 17A to 17F represent amplifiers provided to render the gains for respective colors to be variable. Numerals 20A to 20F represent memories. The first dichroic mirror of the three-color spectroscopic prism 36 possesses such a reflection property as shown in FIG. 4A. The second dichroic mirror thereof which transmits therethrough those rays other than that has the reflection property as shown in FIG. 4B and transmits these other rays therethrough. And, in front of the solid-state image sensor 37, there is placed a filter having such a transmittance as shown in FIG. 4C. Whereby, it becomes possible to obtain three primary color signals in the visible light range and false color signals in the infrared light range as in the instance of FIG. 11. The multiplexing gate signal generator 19 functions to effect changeover of connections between the group of switches $SW_1$, $SW_3$ and $SW_5$ and the group of switches $SW_2$, $SW_4$ and $SW_6$ correspondingly to the changeover between visible light and infrared rays performed by the rotatable filter disc 29. The ampliers 17A to 17F are intended to perform fine adjustment of the gains of respective color signals, and they are exactly the same in function as stated earlier. The roles of the memories 20A to 20F are identical with those shown in FIG. 11.

It should be noted here that, in case an infrared ray-visible light changeover filter disc (rotatable filter disc 29) is mounted on the light source side in such a manner as shown in FIG. 11, the infrared light generated at the object under observation will impinge onto the image sensor even when the filter is for visible light. In case, however, this ray-changeover filter disc is provided on the image sensor side, there is performed complete changeover between visible light and infrared light, so that the effect which is obtained will differ somewhat between these two kinds of arrangement. As such, a selective use of arrangement of the ray-changeover filter discs should be made depending on the purposes.

It should be noted here that, in place of the TV camera 35 of either the 3-CCD system or 3-tube system, there may be employed either 1-CCD or 1-tube type TV camera using a mozaic filter.

In the above-described respective embodiments, arrangement is provided so as to effect changeover between two kinds of images by virtue of the combination of visible light R, G and B and infrared light $I_1$, $I_2$ and $I_3$. It should be noted here that the arrangement is not limited thereto, and the combinations of R, G, $I_1$ and B, $I_2$, $I_3$ or the combination of R, $I_1$, $I_2$ and R, $I_3$, G may be used also.

Figure 13:
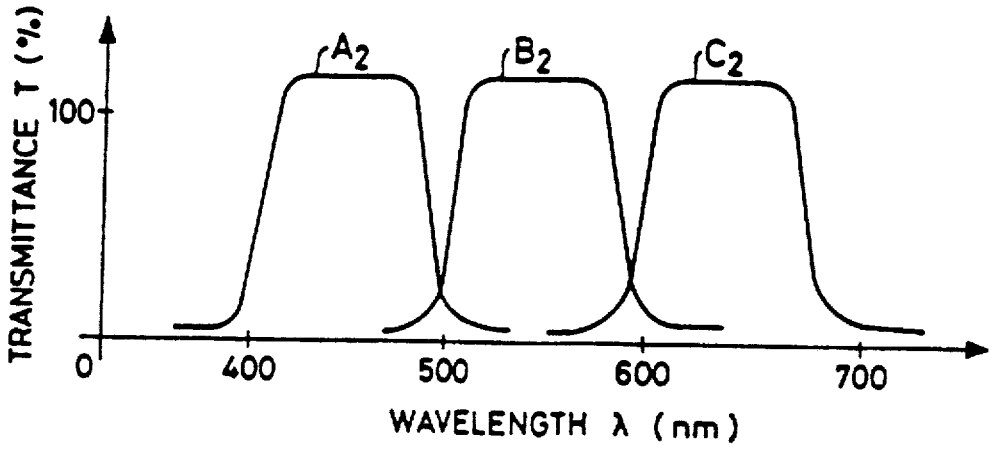
FIGS. 13 to 19 are illustration showing the spectral transmittances of various types of filters, respectively.
Figure 14:
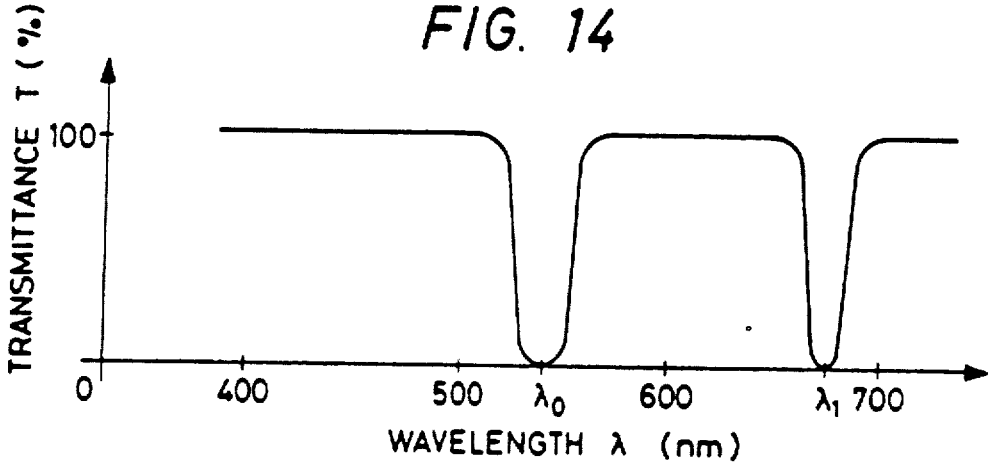
Figure 15:
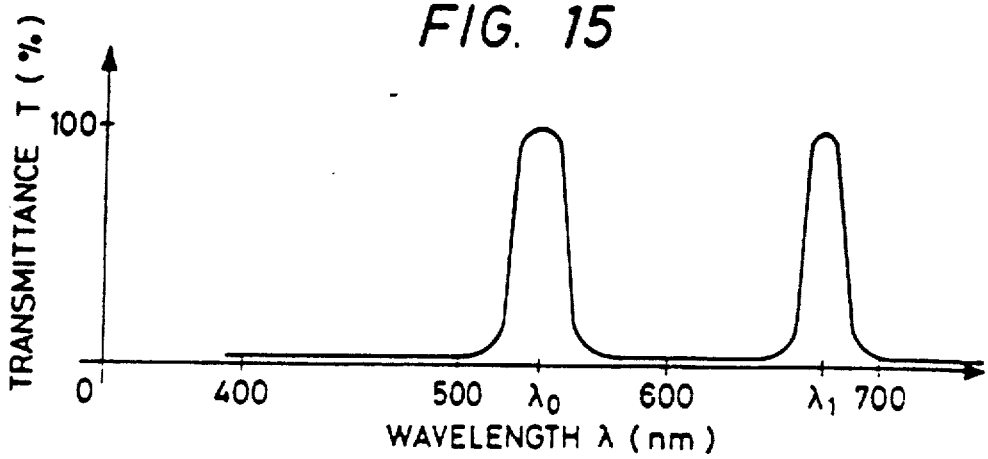

Also, when it is intended to perform an observation of an object having such a spectral distribution as bearing a relatively steep or sharp peak at specific wavelengths $\lambda_0$ and $\lambda_1$ as in blood hemoglobin, the rotatable filter disc 8 to be employed is set to have such properties as $A_2$, $B_2$ and $C_2$ of FIG. 13, and a first filter having such spectral transmittance characteristic bearing a steep or sharp peak at specific wavelengths $\lambda_0$ and $\lambda_1$ as shown in FIG. 15 is arranged to be used instead of the infrared light removing filter 27, whereas a second filter having such spectral transmittance characteristic sharply removing around the specific wavelengths $\lambda_0$ and $\lambda_1$ as shown in FIG. 14 is arranged to be used instead of the visible light removing filter 28, wherein by case the second filter is used, a substantially ordinary visible light is made feasible, whereas in case the first filter is used, it becomes possible to make an observation under lights having wavelength $\lambda_0$ and $\lambda_1$.

Figure 16:
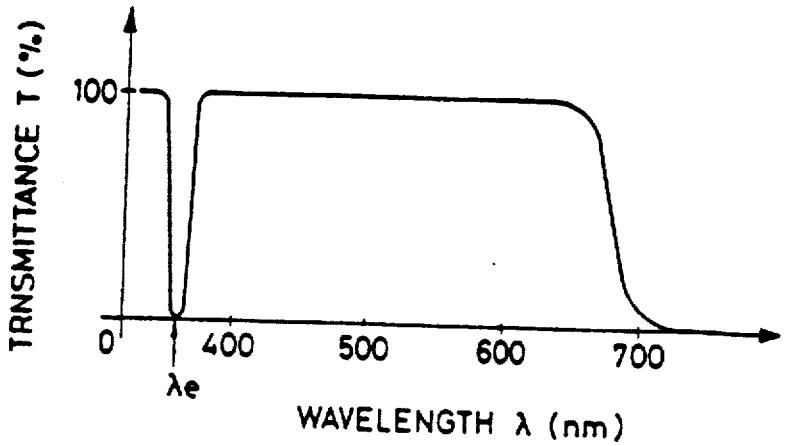
Figure 17:
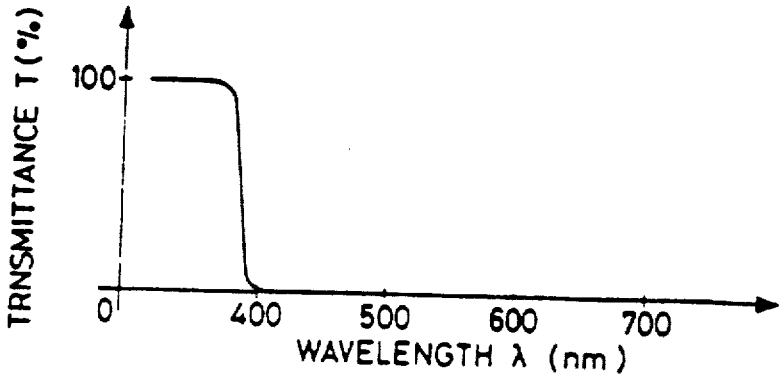

In case of an observation using a fluorescent light, a filter for removing the light for excitation having the wavelength $\lambda_0$ as shown in FIG. 16 and another filter capable of transmitting the light for excitation therethrough but removing the visible light as shown in FIG. 17 are interchangingly inserted in the optical path on the light source side, whereby it is possible to obtain alternating views of the color image of visible light and the image of fluorescent light.

Figure 18:
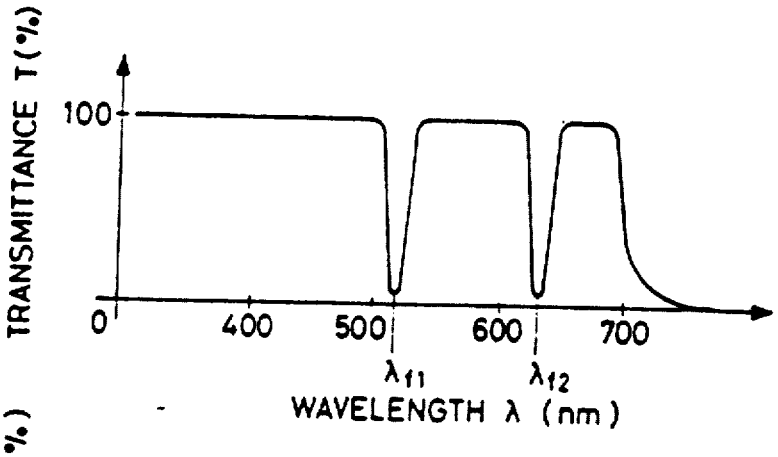
Figure 19:
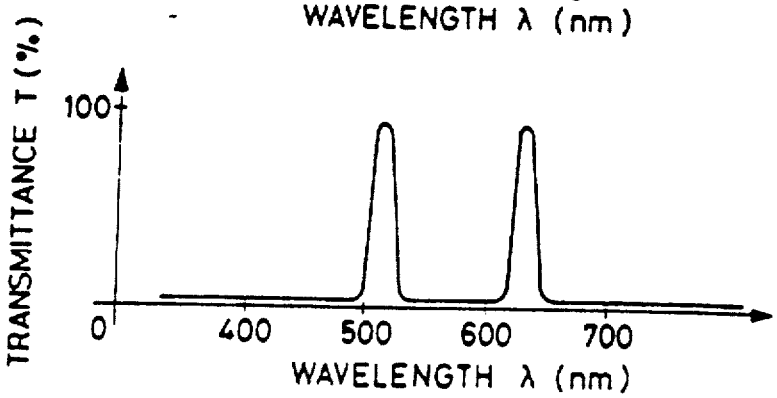

Also, in case of a TV camera (including electronic mechanisms) which is mounted on an endoscope, a filter for removing fluorescent light having wavelengths $f_1$ and $f_2$ as shown in FIG. 18 and a filter which transmits said fluorescent light therethrough but removes visible rays as shown in FIG. 19 are interchangingly inserted in the image pickup optical path of the TV camera, whereby alternating observations of the visible light image and the fluorescent light image can be made. Or, arrangement may be made to that, by using the interference filter having the property of FIG. 18 in its tilted position in the optical path relative to the optical axis, and allowing the passage of lights having the wavelengths $\lambda_{f1}$ and $\lambda_{f2}$ therethrough by shifting the non-transmitting wavelengths from $\lambda_{f1}$ and $\lambda_{f2}$, whereby performing observations utilizing both of the visible light and the fluorescent ray. On the other hand, in case the filter is not tilted, rays having wavelengths $\lambda_{f1}$ and $\lambda_{f2}$ are removed, so that an ordinary observation can be made.

It should be understood here that the wavelengths $\lambda_0$, $\lambda_{f1}$ and $\lambda_{f2}$ may be present in whichever wavelength bands of infrared light and ultraviolet light, and that the number of wavelengths which can be used is not limited.

Figure 20:
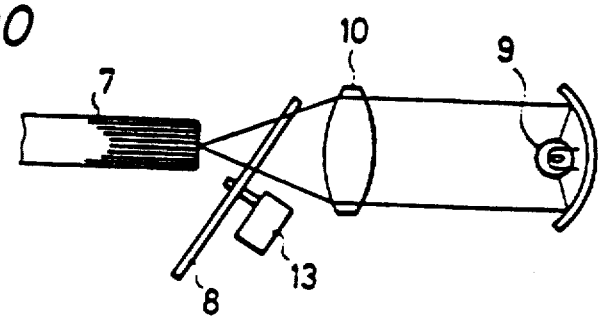
FIG. 20 is an illustration showing the arrangement of the essential portion of a further embodiment wherein a filter disc is disposed in its tilted position relative to the optical axis.
Figure 21:
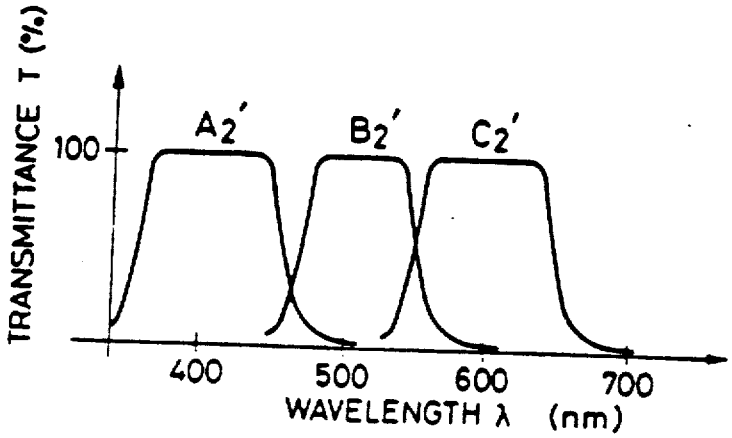
FIG. 21 is an illustration showing the changes, toward the short wavelength region, of the spectral transmittance obtained from the interference filter of FIG. 20 which is tilted relative to the optical axis.
Figure 22:
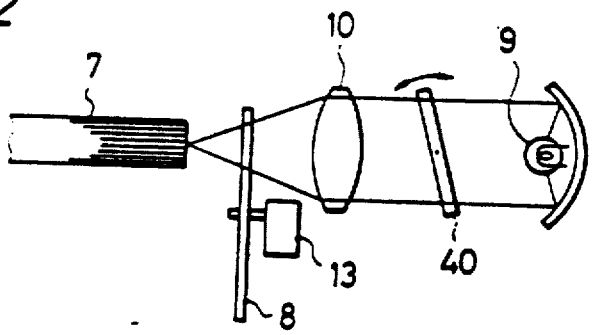
FIG. 22 is an illustration showing the arrangement of the essential part of a still further embodiment wherein a fluorescent light removing filter is disposed in the optical path of the light source means so as to be tiltable relative to the optical axis.
Figure 23:
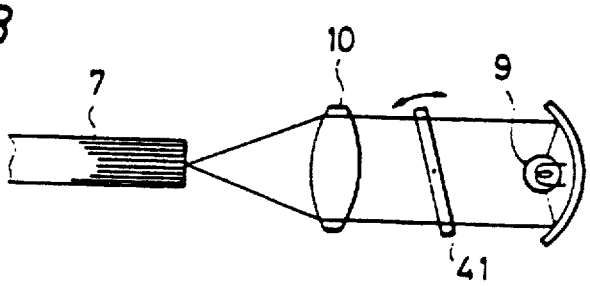
FIG. 23 is an illustration showing the arrangement of the essential part of a yet further embodiment wherein an infrared light removing filter is disposed in the optical path of the light source means so as to be tiltable relative to the optical axis.

The technique of performing an observation of an object while altering the spectral characteristic, i.e. spectral transmittance, of a given illuminating light by tilting such an interference filter as mentioned above relative to the optical axis can be accomplished also in the embodiment shown in FIG. 1. That is, in case of an arrangement such that the rotatable filter 8 of FIG. 1 is set to possess such a spectral transmittance as that shown in FIG. 13 and that this filter is arranged at right angles relative to the optical axis as shown in FIG. 1, an ordinary color image observation of the object is feasible. However, by tilting this filter 8 relative to the optical axis as shown in FIG. 20, the spectral transmittance of the interference filter with shift toward the short wavelength region, as indicated by $A_2'$, $B_2'$ and $C_2'$ in FIG. 21, so that an observation of a false color image in a different wavelength range is achieved. It should be noted here that, in place of the filter 8, the infrared ray removing filter 27 may be tilted. Furthermore, jointly with this tilting of the filter 27, the gain of the circuitry for each color light may be altered to thereby automatically regulate the balancing of the white color light impinging onto the device. In this latter instance, the visible light removing filter 28 is not provided. Instead, the provision of only the infrared light removing filter 27 is required. That is, in the device provided with a filter in the optical path, it is only necessary to arrange the filter so as to be tiltable relative to the optical axis in such a way that the filter is capable of assuming at least two different angles relative thereto. Accordingly, in case the filter disc 8 is arranged so as to be tilted in a device of the color-sequential system, the above said filters 27 and 28 may both be omitted. Furthermore, in the device of the simultaneous system using a mozaic filter, there may be disposed a filter having a special transmitting wavelength range (e.g. an infrared light removing filter) so as to be tiltable relative to the optical axis. And, in these devices, also which are designed so as to tilt the filter, it is needles to say that a fiberscope may be formed with the illuminating system and the objective lens, and that an image pickup means may be housed in a TV camera which is mounted on the eyepiece of the fiberscope.

Description has been made with respect to the embodiments wherein respective light-transmitting filters are arranged at an equal interval from each other via a light-removing area intervening therebetween. It should be understood, however, that the present invention is not limited to devices having such an arrangement of the filters as mentioned above. There may be devices wherein the filters are not arranged at an equal interval from each other depending on the individual requirements.

What is claimed is:

1. An electronic image pickup device for endoscopes, comprising:

an illuminating system including:

light source means, light-transmitting means having a light-incidence end face abutting said light source means and a light-emitting end face directed to an object under observation to irradiate a light coming from said light source means onto said object, a first filter disc rotatably disposed between said light source means and said light-incidence end face of said light-transmitting means and having light-transmitting areas arranged on a same circumference of said disc via a light-removing area intervening between the respective light-transmitting areas for removing the light coming from said light source means for transmitting at least three different color lights one after another in succession through said light-transmitting areas as said first filter disc is rotated; and an image pickup system disposed in association with said illuminating system and including:

an objective lens, image pickup means for receiving an image of said object formed by said objective lens, and color image display means connected to said image pickup means for producing a color image of said object based on an electric signal supplied from said image pickup means, wherein:

a plurality of filters having mutually different transmitting wavelength ranges are disposed for alternative insertion into an optical path of either one of said illuminating system and said image pickup system, thereby making it possible to obtain a color image by rays of a plurality of wavelength ranges.

2. An electronic image pickup device for endoscopes according to claim 1, wherein:

said three different color lights are red, green and blue in color.

3. An electronic image pickup device for endoscopes according to claim 1, wherein:

said plurality of filters are an infrared light removing filter and a visible light removing filter which are slidably disposed between said light source means and the light-incidence end face of said light-transmitting means.

4. An electric image pickup device for endoscopes according to claim 1, wherein:

said plurality of filters are comprised of an infrared light removing filter, and a complex filter formed by overlapping a visible light removing filter, and another infrared light removing filter to transmit ultraviolet light therethrough, each of said infrared light removing filter and said complete filter being slidably disposed between said light source means and the light-incidence end face of said light-transmitting means.

5. An electronic image pickup device for endoscopes according to claim 3 or 4, wherein:

said image pickup system further comprises an amplifier connected to said image pickup system in association with said plurality of filters and being variable of its gain interlockingly with an insertion of said infrared light removing filter, said visible light removing filter or said complex filter into said optical path.

6. An electronic image pickup device for endoscopes according to claim 3 or 4, wherein:

said image pickup means is movably provided along said optical path in association with said plurality of filters, and arranged to move said image pickup means interlockingly with the insertion, into said optical path, of either said infrared light removing filter, said visible light removing filter or said complex filter in order to bring the light-receiving face of said image pickup means into the focusing position of an image produced by visible light, infrared ray or ultraviolet ray.

7. An electronic image pickup device for endoscopes according to claim 3, wherein:

said objective lens is provided to be movable along said optical path and is moved interlockingly with an insertion, into said optical path, of said infrared light removing filter or said visible light removing filter in order to bring the light-receiving face of said image pickup means into a focusing position of an image produced by visible light or infrared light.

8. An electronic image pickup device for endoscopes according to claim 4, wherein:

said objective lens is provided to be movable along said optical path and is moved interlockingly with an insertion, into said optical path, of said infrared ray removing filter, said visible ray removing filter or said complex filter in order to bring the light-receiving face of said image pickup means into a focusing position of an image produced by visible ray, infrared ray or ultraviolet ray.

9. An electronic image pickup device for endoscopes according to claim 1, wherein:

said plurality of filters are comprised of an infrared light removing filter and a visible ray removing filter, said infrared light removing filter and said visible light removing filter are disposed via a light-removing area intervening between the respective filters, on a same circumference of a second filter disc rotatably disposed between said light source means and said lighttransmitting means, said second filter disc is arranged to be rotated at a revolution speed which is ½ of that of said first filter disc, and said color image display means is constituted by a pair of color TV monitoring means and is coupled to said image pickup means via a pair of switch means which are changed over of their connections interlockingly with a revolution of said second filter disc, whereby by operating said pair of switch means in synchronism with the revolutions of said second filter disc, there can be obtained simultaneously a visible light color image and an infrared light false color image via said pair of color TV monitoring means.

10. An electronic image pickup device for endoscopes according to claim 1, wherein:

said objective lens is built in a distal end of said endoscope, said endoscope is provided with an image guide fiber bundle receiving on its one end face the object image formed by said objective lens, and an eyepiece for observing the other end face of said image guide fiber bundle, said image pickup means is housed within a TV camera detachably attached on the light emitting side of said eyepiece and is adapted to receive the object image transmitted by said image guide fiber bundle through said eyepiece, and said plurality of filters are an infrared light removing filter and a visible light removing filter which are slidably disposed in the foreground of said image pickup means within said TV camera.

11. An electronic image pickup device for endoscopes according to claim 1, wherein:

said objective lens is built in a distal end of said endoscope, said endoscope is provided with an image guide fiber bundle receiving on its one end face the object image formed by said objectives lens, and an eyepiece for observing the other end face of said image guide fiber bundle, said image pickup means is housed within a TV camera detachably attached on the light emitting side of said eyepiece and is adapted to receive the object image transmitted by said image guide fiber bundle through said eyepiece, said plurality of filters are an infrared light removing filter and a visible removing filter which are disposed via a light-removing area intervening therebetween on a same circumference of a second filter disc rotatably disposed in the foreground of said image pickup means provided within said TV camera, and said second filter disc is rotated at a revolution speed which is ½ of that of said first filter disc.

12. An electronic image pickup device for endoscopes according to claim 10 or 11, wherein:

said image pickup means is comprised of a plurality of solid-state image sensors which are disposed for alternative insertion into said optical path and have mutually different light-sensitive wavelength ranges.

13. An electronic image pickup device for endoscope according to claim 1, wherein:

said plurality of filters are comprised of filter removing light for excitation and a filter transmitting light for excitation therethrough but removing visible light.

14. An electronic image pickup device for endoscopes according to claim 1, wherein:

said objective lens is built in a distal end of said endoscope, said endoscope is provided with an image guide fiber bundle receiving on its one end face the object image formed by said objective lens, and an eyepiece for observing the other end face of said image guide fiber bundle, said image pickup means is housed with a TV camera detachably attached on the light emitting side of said eyepiece and is adapted to receive the object image transmitted by said image guide fiber bundle through said eyepiece said plurality of filters are comprised of a filter for removing fluorescent light and a filter for transmitting fluorescent light therethrough but removing visible, light both of which filters being slidably disposed in the foreground of said image pickup means housed in said TV camera.

15. An electronic image pickup device for endoscopes according to claim 1, wherein:

said objective lens is built in a distal end of said endoscope, said endoscope is provided with an image guide fiber bundle receiving on its one end face the object image formed by said objective lens, and an eyepiece for observing the other end face of said image guide fiber bundle, said image pickup means is housed with a TV camera detachably attached on the light emitting side of said eyepiece and is adapted to receive the object image transmitted by said image guide fiber bundle through said eyepiece, said plurality of filters are comprised of a filter removing fluorescent light and a filter transmitting fluorescent light therethrough but removing visible rays both of which filters being arranged via a light-removing area intervening therebetween on a same circumference of a second filter disc rotatably disposed in the foreground of said image pickup means provided within said TV camera, and said second filter disc is rotated at a revolution speed which is ½ of that of said first filter disc.

16. An electronic image pickup device for endoscope according to claim 3, wherein:

said image pickup system further comprises an amplifier connected to said image pickup system in association with said plurality of filters and being variable of its gain interlockingly with an insertion of said infrared light removing filter or said visible light removing filter into said optical path, and said objective lens is built in a distal end of said endoscope, said endoscope is provided with an image guide fiber bundle receiving on its one end face the object image formed by said objective lens, and an eyepiece for observing the other end face of aid image guide fiber bundle, said image pickup means is housed with a TV camera detachably attached on the light emitting side of said eyepiece and is adapted to receive the object image transmitted by said image guide fiber bundle through said eyepiece, and said plurality of filters are slidably disposed in the foreground of said image pickup means provided within said TV camera.

17. An electronic image pickup device for endoscope according to claim 4, wherein:

said image pickup system further comprising an amplifier connected to said image pickup system in association with said plurality of filters and being variable of its gain interlocking with an insertion of said infrared light removing filter, said visible light removing filter or said complex filter into said optical path, said objective lens is built in a distal end of said endoscope, said endoscope is provided with an image guide fiber bundle receiving on its one end face the object image formed by said objective lens, and an eyepiece for observing the other end face of said image guide fiber bundle, said image pickup means is housed within a TV camera detachably attached on the light emitting side of said eyepiece and is adapted to receive the object image transmitted by said image guide fiber bundle through said eyepiece, and said plurality of filters including said complex filter are slidably disposed in the foreground of said image pickup means provided within said TV camera.

18. An electronic image pickup device for endoscopes according to claim 3, wherein:

said image pickup means is movably provided along said optical path in association with said plurality of filters, and arranged so that said image pickup means is moved interlockingly with the insertion, into said optical path, of either said infrared light removing filter or said visible light removing filter in order to bring the light-receiving face of said image pickup means into focusing position of an image produced by visible light or infrared light, said objective lens is built in a distal end of said endoscope, said endoscope is provided with an image guide fiber bundle receiving on its one end face the object image formed by said objective lens, and an eyepiece for observing the other end face of said image guide fiber bundle, said image pickup means is housed with a TV camera detachably attached on the light emitting side of said eyepiece and is adapted to receive the object image transmitted by said image guide fiber bundle through said eyepiece, and said plurality of filters are slidably disposed in the foreground of said image pickup means provided within said TV camera.

19. An electronic image pickup device for endoscopes according to claim 4, wherein:

said image pickup means is movably provided along said optical path in association with said plurality of filters, and arranged so that said image pickup means is moved interlockingly with the insertion, into said optical path, of either said infrared light removing filter, said visible light removing filter or said complex filter in order to bring the light-receiving face of said image pickup means into the focusing position of an image produced by visible light, infrared light or ultraviolet light, said objective lens is built in a distal end of said endoscope, said endoscope is provided with an image guide fiber bundle receiving on its one end face the object image formed by said objective lens, and an eyepiece for observing the other end face of said image guide fiber bundle, said image pickup means is housed with a TV camera detachably attached on the light emitting side of said eyepiece and is adapted to receive the object image transmitted by said image guide fiber bundle through said eyepiece, and said complex filter is slidably disposed in the foreground of said image pickup means provided within said TV camera.

20. An electronic image pickup divide for endoscopes according to claim 3, wherein:

said objective lens is provided to be movable along said optical path and is moved interlockingly with an insertion, into said optical path, of said infrared light removing filter or said visible light removing filter in order to bring the light-receiving face of said image pickup means into a focusing position of an image produced by visible light or infrared light, said objective lens is built in a distal end of said endoscope, said endoscope is provided with an image guide fiber bundle receiving on its one end face the object image formed by said objective lens, and an eyepiece for observing the other end face of said image guide fiber bundle, said image pickup means is housed with a TV camera detachably attached on the light emitting side of said eyepiece and is adapted to receive the object image transmitted by said image guide fiber bundle through said eyepiece, and said plurality of filters are disposed slidably in the foreground of said image pickup means provided within said TV camera.

21. An electronic image pickup device for endoscopes according to claim 4, wherein:

said objective lens is provided to be movable along said optical path and is moved interlockingly with a n insertion, into said optical path, of said infrared light removing filter, or said visible light removing filter or said complex filter in order to bring the light-receiving face of said image pickup means into a focusing position of an image produced by visible light, infrared light or ultraviolet light, said objective lens is built in a distal end of said endoscope, said endoscope is provided with an image guide fiber bundle receiving on its one end face the object image formed by said objective lens, and an eyepiece for observing the other end face of said image guide fiber bundle, said image pickup means is housed with a TV camera detachably attached on the light emitting side of said eyepiece and is adapted to receive the object image transmitted by said image guide fiber bundle through said eyepiece, and said complex filter is slidably disposed in the foreground of said image pickup means provided within said TV camera.

22. An electronic image pickup device for endoscopes according to claim 1, wherein:

said plurality of filters are comprised of a filter removing light for excitation and a filter transmitting light for excitation therethrough but removing visible light, said objective lens is built in a distal end of said endoscope, said endoscope is provided with an image guide fiber bundler receiving on its one end face with the object image formed by said objective lens, and an eyepiece for observing the other end face of said image guide fiber bundle, said image pickup means is housed with a TV camera detachably attached on the light emitting side of said eyepiece and is adapted to receive the object image transmitted by said image guide fiber bundle through said eyepiece, and said plurality of filters are disposed in the foreground of said image pickup means provided within said TV camera.

23. An electronic image pickup device for endoscopes according to claim 1, wherein:

said plurality of filters are comprises of a filter removing light for excitation and a filter transmitting light for excitation therethrough but removing visible light, said objective lens is built in a distal end of said endoscope, said endoscope is provided with an image guide fiber bundle receiving on its one end face the object image formed by said objective lens, and an eyepiece for observing the other end face of said image guide fiber bundle, said image pickup means is housed with a TV camera detachably attached on the light emitting side of said eyepiece and is adapted to receive the object image transmitted by said image guide fiber bundle through said eyepiece, and said plurality of filters are slidably disposed in the foreground of said image pickup means housed within said TV camera.

24. An electronic image pickup device for endoscopes, comprising:

an illuminating system including:

light source means, and light-transmitting means having a light-incidence end face abutting said light source means and a light emitting end face directed to an object under observation to irradiate a light coming from said light source means onto said object; and an image pickup system including:

an objective lens, image pickup means having a color encoding filter at its light-receiving face and receiving an image of said object formed by said objective lens, and color image display means connected to said image pickup means for producing a color image of said object based on an electric signal supplied from said image pickup means, wherein:

a plurality of filters having mutually different transmitting wavelength ranges are disposed for alternative insertion into an optical path of either one of said illuminating system and said image pickup system, whereby making it possible to obtain a color image by rays of a plurality of wavelength ranges.

25. An electronic image pickup device for endoscopes according to claim 24, wherein:

said plurality of filters are comprised of a filter removing light for excitation and a filter transmitting light for excitation therethrough but removing said visible light.

26. An electric image pickup device for endoscopes according to claim 24, wherein:

said objective lens is built in a distal end of said endoscope, said endoscope is provided with an image guide fiber bundle receiving on its one end face the object image formed by said objective lens and transmitting the object image onto its other end face, and said image pickup means is adapted to receive the object image transmitted through said image guide fiber bundle.

27. An electronic image pickup device for endoscopes, comprising:

an illuminating system including:

light source means, light-transmitting means having a light-incidence end face abutting said light source means and a light-emitting end face directed to an object under observation to irradiate a light coming from said light source means onto said object, a filter disc rotatably disposed between said light source means and said light-incidence end face of said light-transmitting means and having two filters possessing mutually different transmitting wavelength ranges and being arranged on said circumference via a light-removing area intervening between the respective filters; and an image pickup system disposed in association with said illuminating system and including:

an objective lens, image pickup means having a color encoding filter formed on its light-receiving face and receiving an image of said object formed by said objective lens, a pair of switch means connected to said image pickup means and being changed over of their connection interlockingly with a revolution of said filter disc, and a pair of TV monitoring means connected to said pair of switch means, respectively, wherein:

said pair of switch means are operated alternatingly in synchronism with a changeover between said two filters from one to the other which are to be inserted into an optical path by a revolution of said filter disc, whereby realizing simultaneous display of two different kinds of color images produced by rays having mutually different wavelength ranges.

28. An electronic image pickup device for endoscopes according to claim 27, wherein:

said two filters are comprised of an infrared light removing filter and a visible light removing filter.

29. An electronic image pickup device for endoscopes, comprising:

an illuminating system including:

light source means, and light-transmitting means having a light-incidence end face abutting said light source means and a light-emitting end face directed to an object under observation to irradiate a light coming from said light source means onto said object;

an endoscope provided with with said light-transmitting means, an objective lens and a light guide for transmitting an image of said object formed by said objective lens to a predetermined position;

a TV camera having:

a photographic lens and a three color separating prism assembly disposed on the light emitting side of said light guide; and three image pickup means respectively disposed to face respective light-emitting end faces of said prism assembly and a filter disc rotatably disposed between said photographic lens and said prism assembly and having two filters possessing mutually different transmitting wavelength ranges and being arranged on a same circumference of said disc via a light-removing area intervening therebetween;

three pairs of switch means connected to said image pickup means, respectively, and comprised of a first switch group and a second switch group which are arranged over of their connections interlockingly with a revolution of said filter disc;

a first color TV monitoring means connected to said first switch group o said three pairs of switch means; and a second color TV monitoring means connected to said second switch group of said three pairs of switch means, wherein:

said first switch group and said second switch group of said three pairs of switch means are alternating operated in synchronism with a changeover between said two filters from one to the other which are to be inserted into an optical path by a revolution of said filter disc, thereby realizing a simultaneous display of two different kinds of color images produced by lights possessing mutually different wavelength ranges.

30. An electronic image pickup device for endoscopes according to claim 29, wherein:

said two filters are comprised of an infrared light removing filter and a visible light removing filter.

31. An electronic image pickup device for endoscopes according to claim 29, wherein:

said two filters are comprised of a filter for removing fluorescent light and a filter for transmitting fluorescent light therethrough but removing visible light.

32. An electronic image pickup device for endoscopes, comprising:

an illuminating system including:

light source means, light-transmitting means having a light-incidence end face abutting said light source means and a light emitting end face directed to an object under observation to irradiate a light coming from said light source means onto said object, a filter disc rotatably disposed between said light source means and said light-incidence end face of said light-transmitting means and having light-transmitting areas arranged on a same circumference of said disc via a light-removing area intervening between the respective light-transmitting areas for removing the light coming from said light source means for transmitting at least three different color lights one after another in succession through said light-transmitting areas as said filter disc is rotated; and an image pickup system disposed in association with said illuminating system and including:

an objective lens, image pickup means for receiving an image of said object formed by said objective lens, and color image display means connected to said image pickup means for producing a color image of said object based on an electric signal supplied from said image pickup means, wherein:

said filter disc is arranged to be tiltable relative to an optical axis in said optical path to thereby be able to obtain a color image of said object formed by rays having a plurality of wavelength ranges.

33. An electronic image pickup device for endoscopes according to claim 32, wherein:

said objective lens is built in a distal end of said endoscope, said endoscope is provided with an image guide fiber bundle receiving on its one end face the object image formed by said objective lens, and an eyepiece for observing the other end face of said image guide fiber bundle, and said image pickup means is housed within a TV camera detachably attached on the light emitting side of said eyepiece and is adapted to receive the object image transmitted by said image guide fiber bundle through said eyepiece.

34. An electronic image pickup device for endoscopes, comprising:

an illuminating system including:

light source means, light-transmitting means having a light-incidence end face abutting said light source means and a light emitting end face directed to an object under observation to irradiate a light coming from said light source means onto said object, a first filter disc rotatably disposed between said light source means and said light-incidence end face of said light-transmitting means and having lighttransmitting areas arranged on a same circumference of said disc via a light-removing area intervening between the respective light-transmitting areas for removing the light coming from said light source means for transmitting at least three different color lights one after another in succession through said light-transmitting areas as said first filter disc is rotated; and an image pickup system disposed in association with said illuminating system and including:

an objective lens, image pickup means for receiving an image of said object formed by said objective lens, and color image display means connected to said image pickup means for producing a color image of said object based on an electric signal supplied from said image pickup means, wherein:

a second filter disc having areas of specific transmitting wavelength ranges is disposed in the optical path of either said illuminating system or said image pickup system, and either one of said first filter disc and said second filter disc is arranged to be tiltable relative to an optical axis of either one of said optical paths.

35. An electronic image pickup divide for endoscopes according to claim 32, wherein:

said objective lens is built in a distal end of said endoscope, said endoscope is provided with an image guide fiber bundle receiving on its one end face the object image formed by said objective lens, and an eyepiece for observing the other end face of said image guide fiber bundle, and said image pickup means is housed within a TV camera detachably attached on the light emitting side of said eyepiece and is adapted to receive the object image transmitted by said image guide fiber bundle through said eyepiece.

36. An electronic image pickup device for endoscopes, comprising:

an illuminating system including:

light source means, and light-transmitting means having a light-incidence end face abutting said light source means and a light-emitting end face directed to an object under observation to irradiate a light coming from said light source means onto said object; and an image pickup system including:

an objective lens, image pickup means having a color encoding filter at its light-receiving face and receiving an image of said object formed by said objective lens, and color image display means connected to said image pickup means for producing a color image of said object based on an electric signal supplied from said image pickup means, wherein:

a filter having a specific transmitting wavelength range is disposed in the optical path of either one of said illuminating system and said image pickup system, and said filter is arranged to be tiltable relative to an optical axis of the optical path of either one of said systems.

37. An electronic image pickup device for endoscopes according to claim 36, wherein:

said objective lens is built in a distal end of said endoscope, said endoscope is provided with an image guide fiber bundle receiving on its one end face the object image formed by said objective lens, and an eyepiece for observing the other end face of said image guide fiber bundle, and said image pickup means is housed within a TV camera detachably attached on the light emitting side of said eyepiece and is adapted to receive the object image transmitted by said image guide fiber bundle through said eyepiece.

38. An electrical image pickup device for endoscopes, comprising:

an illuminating system including:

light source means, light guide means receiving a light coming from said light source means to irradiate the light onto an object under observation, means disposed between said light source means and said light guide means to enter three different color lights included in the light coming form said light source means on after another in succession into said light guide means; and an image pickup system disposed in association with said illuminating system and including:

an objective lens, image pickup means for receiving an image of said object formed by said objective lens, and color image display means connected to said image pickup means for producing a color image of said object based on an electric signal supplied from said image pickup means, wherein:

a plurality of filters having mutually different transmitting wavelength ranges are disposed for alternative insertion into an optical path of either one of said illuminating system and said image pickup system, thereby making it possible to obtain a color image by rays of a plurality of wavelength ranges.

39. An electronic image pickup device for endoscopes, comprising:

an illuminating system including:

light source means, light guide means receiving a light coming from said light source means to irradiate the light onto an object under observation, means disposed between said light source means and said light guide means to enter three different color lights included in the light coming from said light source means one after another in succession into said light guide means; and an image pickup system disposed in association with said illuminating system and including:

an objective lens, an image guide means transmitting an image of said object formed by said objective lens to a predetermined position, an image pickup means receiving the object image transmitted by said image guide means, and color image display means connected to said image pickup means for producing a color image of said object based on an electric signal supplied from said image pickup means, wherein:

a plurality of filters having mutually different transmitting wavelength ranges are disposed for alternative insertion into an optical path of either one of said illuminating system and said image pickup system, whereby making it possible to obtain a color image by rays of a plurality of wavelength ranges.

*40. An imaging apparatus comprising:*

*an illuminating means for emitting illuminating light of a wavelength range including a visible range and another range other than the visible range;*

*an image forming optical system, disposed in association with said illuminating means, for forming the image of an object to be imaged;*

*an imaging means having a sensitivity to a wavelength range ranging from a visible range to another range than the visible range and converting the image formed by said image forming optical system to an electric signal;*

*a wavelength range dividing means dividing the wavelength range into the visible range and another range than the visible range to provide a plurality of wavelength ranges;*

*a selecting means selecting at least one wavelength range from among the wavelength ranges divided by said wavelength range dividing means; and*

*signal processing means processing the output signals of said imaging means, in response to said selected wavelength ranges, into video signals.*

*41. An imaging apparatus comprising:*

*an illuminating means for emitting illuminating light of a wavelength range including a visible range and another range other than the visible range;*

*an image forming optical system disposed in association with said illuminating means, for forming an image of an object to be imaged;*

*an imaging means having a sensitivity to a wavelength range ranging from a visible range to the another range than the visible range and converting the image formed by said image forming optical system to an electric signal;*

*a separating means separating the wavelength range into the visible range and the other range than the visible range and having a plurality of kinds of optical members having a characteristic of respectively transmitting or reflecting and separating the light of a specific wavelength range within a visible band and another band than the visible band;*

*a band limiting means limiting the separated wavelength ranges of the respective optical members of said separating means to either band to select the wavelength range imaged by said imaging means; and*

*a signal processing means processing the output signals of said imaging means in response to the wavelength ranges selected by said band limiting means so as to be video signals.*

*42. An imaging apparatus comprising:*

*an image forming optical system forming the image of an object to be imaged;*

*an imaging means having a sensitivity to a wavelength range ranging from a visible range to another range than the visible range and converting the image formed by said image forming optical system to an electric signal;*

*a wavelength range dividing means dividing the wavelength range of an illuminating light into a plurality of wavelength ranges within the range to which said imaging means has its sensitivity and capable of dividing in time series the illuminating light with a combination of at least a part of said plurality of wavelength ranges;*

*a selecting means selecting at least one wavelength range from among the wavelength ranges divided by said wavelength range dividing means; and*

*a signal processing means processing the output signals of said imaging means to be a video signal in response to the wavelength range selected by said selecting means.*

*43. An imaging apparatus comprising:*

*an illuminating means capable of emitting an illuminating light of a wavelength range ranging from a visible range to another range than the visible range;*

*an image forming optical system forming the image of an object to be imaged;*

*an imaging means having a sensitivity to a wavelength range from a visible range to another range than the visible range and using a solid state imaging device converting the image formed by said image forming optical system to an electric signal;*

*a filter separating in time series the wavelength range of the illuminating light of said illuminating means into a plurality of wavelength ranges within the ranges to which said imaging means has a sensitivity and having a plurality of kinds of components filters having a transmitting characteristic of transmitting respectively the lights of specific wavelength ranges within a visible band and another band than the visible band;*

*a band limiting means limiting the transmitted wavelength ranges of the respective component filters of said filter to either band to select the wavelength range imaged by said imaging means; and*

*a signal processing means processing the output signals of said imaging means corresponding to the illuminating lights of the wavelength ranges selected by said*

*band limiting by allotting them to respective different color signals so as to be video signals.*

*44. An imaging apparatus according to claim 43 wherein the respective component filters of said filter have respectively different transmitted wavelength ranges within the visible band and the same transmitted wavelength ranges within the infrared band and said band limiting means is a filter transmitting selectively the visible band and infrared band.*

*45. An imaging apparatus according to claim 43 wherein the respective component filters of said filter have respectively different transmitted wavelength ranges in the visible band and infrared band and said band limiting means is a filter transmitting selectively the visible band and infrared band.*

*46. A method of observing an object image of ordinary light and an object image of particular light, comprising the steps of:*

*emitting an illuminating light of a wavelength range ranging from a visible range to a range other than the visible range;*

*dividing the illuminating light emitted by said step of emitting into a plurality of wavelength ranges to obtain the object image of ordinary light or particular light;*

*separating at least one of the plurality of wavelength ranges by said step of dividing into a further plurality of wavelength ranges;*

*illuminating the lights of the wavelength ranges separated by said step of separating to an object;*

*converting said object image illuminated light by said step of illuminating into an electric signal; and*

*imaging the electric signal obtained by said step of converting.*

*47. A method of observing an object image of ordinary light and an object image of particular light, comprising the steps of:*

*emitting an illuminating light of a wavelength range ranging from a visible range to a range other than the visible range;*

*dividing the illuminating light emitted by said step of emitting into a plurality of wavelength ranges to obtain the object image of ordinary light or particular light;*

*illuminating a light of a wavelength range from among the wavelength ranges divided by said step of dividing to an object;*

*separating the object image illuminated by said step of illuminating into a further plurality of images of wavelength ranges;*

*converting the images of the wavelength ranges separated by said step of separating into an electric signal; and*

*imaging the electric signal obtained by said step of converting.*

*48. An imaging apparatus according to any one of claims 40 to 45 further comprising a filter means transmitting only light belonging to a narrow wavelength band from among said illuminating light.*

* * * * *